United States Patent
Chen et al.

(10) Patent No.: US 11,985,995 B2
(45) Date of Patent: May 21, 2024

(54) METHODS OF FREEZE DRYING COMPOSITIONS CONTAINING REBAUDIOSIDE M AND REBAUDIOSIDE D

(71) Applicant: The Coca-Cola Company, Atlanta, GA (US)

(72) Inventors: Youlung Chen, Marietta, GA (US); Xiaoliang Tan, Marietta, GA (US); Indra Prakash, Alpharetta, GA (US); Josef Klucik, Marietta, GA (US); Gil Ma, Atlanta, GA (US); Youngsuk Heo, Cumming, GA (US)

(73) Assignee: The Coca-Cola Company, Atlanta, GA (US)

(*) Notice: Subject to any disclaimer, the term of this patent is extended or adjusted under 35 U.S.C. 154(b) by 585 days.

(21) Appl. No.: 16/300,302

(22) PCT Filed: May 10, 2017

(86) PCT No.: PCT/US2017/031892
§ 371 (c)(1),
(2) Date: Nov. 9, 2018

(87) PCT Pub. No.: WO2017/196933
PCT Pub. Date: Nov. 16, 2017

(65) Prior Publication Data
US 2020/0178587 A1 Jun. 11, 2020

Related U.S. Application Data

(60) Provisional application No. 62/334,201, filed on May 10, 2016.

(51) Int. Cl.
A23L 27/30 (2016.01)
A23L 2/60 (2006.01)
A23L 3/44 (2006.01)

(52) U.S. Cl.
CPC ............... *A23L 27/36* (2016.08); *A23L 2/60* (2013.01); *A23L 3/44* (2013.01)

(58) Field of Classification Search
CPC ............... A23L 27/36; A23L 2/60; A23L 3/44
See application file for complete search history.

(56) References Cited

U.S. PATENT DOCUMENTS

| 5,843,347 A | 12/1998 | Nguyen et al. |
| 5,972,120 A * | 10/1999 | Kutowy ............... A23L 27/36 127/34 |
| 2014/0099403 A1 | 4/2014 | Prakash et al. |
| 2014/0171519 A1 | 6/2014 | Prakash et al. |
| 2014/0357588 A1 | 12/2014 | Markosyan et al. |
| 2015/0017284 A1 | 1/2015 | Prakash et al. |

FOREIGN PATENT DOCUMENTS

| WO | WO 2014/098833 | 6/2014 |
| WO | WO 2017/120480 | 7/2017 |

OTHER PUBLICATIONS

International Search Report from PCT/US2017/031892, issued Aug. 11, 2017.
European Search Report from EP 19129913.0 issued Feb. 6, 2020.
Mani Upreti et al: "Solubility Enhancement of Steviol Glycosides and Characterization of Their Inclusion Complexes with Gamma-Cyclodextrin", International Journal of Molecular Sciences, vol. 12, No. 12, Dec. 3, 2011 (Dec. 3, 2011), pp. 7529-7553.

* cited by examiner

*Primary Examiner* — Jeffrey P Mornhinweg
(74) *Attorney, Agent, or Firm* — King & Spalding

(57) ABSTRACT

Methods of preparing freeze dried powders comprising rebaudioside M and rebaudioside D are provided herein. The freeze dried powders produced by the disclosed methods exhibit improved aqueous solubility over known forms and compositions of rebaudioside M and rebaudioside D. Methods of preparing consumables, e.g. beverages, with the freeze dried compositions are also detailed herein.

15 Claims, No Drawings

METHODS OF FREEZE DRYING COMPOSITIONS CONTAINING REBAUDIOSIDE M AND REBAUDIOSIDE D

CROSS REFERENCE TO RELATED APPLICATIONS

The present application is a national stage application under 35 U.S.C. § 371 of International Application No. PCT/US2017/031892, filed May 10, 2017, which claims priority to U.S. Provisional Application No. 62/334,201, filed May 10, 2016. The complete disclosure of each of the above-identified applications is fully incorporated herein by reference.

FIELD OF THE INVENTION

The present invention relates generally to methods of preparing compositions comprising rebaudioside M ("Reb M") and rebaudioside D ("Reb D") utilizing freeze drying. The freeze dried compositions produced by the disclosed methods exhibit improved aqueous solubility over known forms and compositions comprising Reb M and Reb D. The present invention also relates to methods for preparing consumables, e.g. beverages, comprising the freeze dried compositions.

BACKGROUND OF THE INVENTION

*Stevia* is the common name for *Stevia rebaudiana* (Bertoni), a perennial shrub of the Asteracae (Compositae) family native to Brazil and Paraguay. *Stevia* leaves, the aqueous extract of the leaves, and purified steviol glycosides isolated from *Stevia* have been developed as sweeteners desirable as both non-caloric and natural in origin. Steviol glycosides isolated from *Stevia rebaudiana* include stevioside, rebaudioside A, rebaudioside C, dulcoside A, rubusoside, steviolbioside, rebaudioside B, rebaudioside D and rebaudioside F.

Reb M (also called rebaudioside X), (13-[(2-O-β-D-glucopyranosyl-3-O-β-D-glucopyranosyl-β-D-glucopyranosyl) oxy] ent kaur-16-en-19-oic acid-[(2-O-β-D-glucopyranosyl-3-O-β-D-glucopyranosyl-3-D-glucopyranosyl) ester], was isolated from *Stevia rebaudiana* and characterized:

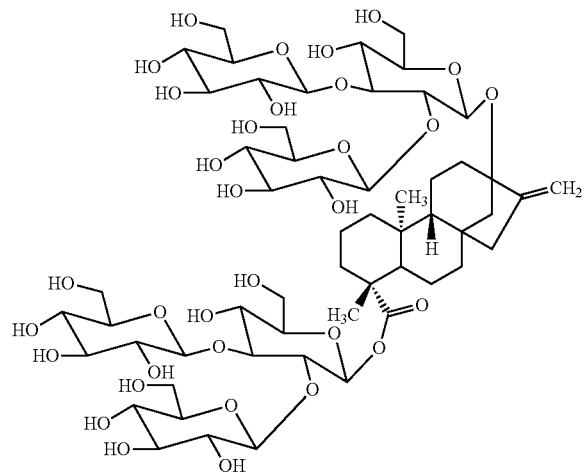

Many steviol glycosides are present in minute quantities in *Stevia rebaudiana*, including Reb M which represents only about 0.05%-0.5% by weight of the leaf. Recently, it was found that Reb M could be used as a sweetener for beverages.

A concentration of at least 0.3% (% w/w) is useful for preparation of syrup and beverage formulations. However, unlike the traditionally used steviol glycoside Rebaudioside A, crystalline compositions containing Reb M and Reb D have poor aqueous solubility and dissolution qualities in beverage formulations. For example, certain crystalline compositions containing about 75-90% Reb M and about 25-10% Reb D by weight cannot be dissolved above concentrations of 0.1-0.15% (% w/w) at room temperature.

Attempts to improve solubility of Reb D include heating highly concentrated solutions to elevated temperatures followed by spray drying (US 20110189360). The concentrated solutions are typically maintained at an elevated temperature during spray drying. Sustained heating leads to degradation and lot-to-lot inconsistency (including poor yields), thereby limiting product quality (including flavor profile) and utilization of spray dried products in commercial use.

Accordingly, there remains a need for improved processes to prepare compositions containing Reb M and Reb D that have aqueous solubilities useful for, e.g. beverage formulations, with predictable, reproducible results and without negatively affecting flavor properties of the compositions.

SUMMARY OF THE INVENTION

The present invention generally relates to methods of preparing freeze dried powders with improved aqueous solubility comprising:
  a. combining (i) a crystalline composition comprising Reb M and Reb D and (ii) water to provide a mixture;
  b. heating the mixture to provide a solution; and
  c. freeze drying the solution to provide a freeze dried powder comprising Reb M and Reb D.

The crystalline composition primarily contains Reb M and Reb D. In exemplary embodiments, both Reb M and Reb D are present in greater than about 10% by weight of the composition. In a particular embodiment, the crystalline composition comprises at least about 75% Reb M by weight and at least about 10% Reb D by weight. In another particular embodiment, the crystalline composition comprises from about 20% to about 30% Reb M by weight and from about 60% to about 70% Reb D by weight. In still another particular embodiment, the crystalline composition comprises rebaudiosides D, M, A, N, O and E, wherein the total steviol glycoside content is about 95% or greater by weight on a dry basis, wherein Reb D accounts for from about 55% to about 70% of the total steviol glycoside content by weight, Reb M accounts for from about 8% to about 30% total steviol glycoside content by weight, rebaudioside A accounts for from about 0.5% to about 4% of the steviol glycoside content by weight, rebaudioside N accounts for from about 0.5% to about 5% of the steviol glycoside content by weight, rebaudioside O accounts for from about 0.5% to about 5% of the total steviol glycoside content by weight and rebaudioside E accounts for from about 0.2% to about 2% of the total steviol glycoside content by weight The mixture can be heated at a time and temperature sufficient to dissolve the crystalline composition and provide a clear solution. In a particular embodiment, the mixture is heated to a temperature from about 70° C. and about 100° C., preferably from about 90° C. to about 100° C.

In certain embodiments, the mixture is heated for from about 1 to about 60 minutes. In exemplary embodiments, sustained heating is minimized to avoid degradation and loss of yield. Accordingly, in particular embodiments, the mixture is heated for about 10 minutes or less, about 5 minutes or less, or about 3 minutes or less.

Once mixture is dissolved in solution, the solution is freeze dried. The freeze drying can be accomplished using, e.g. a liquid nitrogen based technique, to provide frozen pellets, followed by sublimation to provide a freeze dried powder. The freeze dried powder contains substantially similar Reb M and Reb D content as the crystalline composition starting material, i.e. the freeze drying process does not alter the steviol glycoside content by more than 1%.

In large-scale batch methods, the combining step may be conducted in a slurry tank, the heating step can be conducted in a heat exchanger, and the freeze drying step can be conducted in a continuous or batch freeze dryer.

The freeze dried powder produced by these methods has an aqueous solubility of at least 0.5%. Typically, the yield of the process is at least about 85%.

The present invention also provides a freeze dried powder produced by the methods disclosed herein, wherein the powder has an aqueous solubility of at least about 0.5%.

The present invention also provides compositions comprising the freeze dried powder. In one embodiment, a composition comprises a freeze dried powder of the present invention and one or more additional sweeteners, additives and/or functional ingredients.

The present invention also provides consumables prepared with the freeze dried powder. Exemplary consumables include, but are not limited to, pharmaceutical compositions, edible gels and mixes, dental compositions, confections, condiments, chewing gum, cereal compositions, baked goods, dairy products, tabletop sweeteners, beverages and beverage products. In a particular embodiment, the consumable is a beverage or beverage product.

A method of preparing a consumable comprises (i) providing a consumable matrix and (ii) adding a freeze dried powder of the present invention, or a composition comprising a freeze dried powder of the present invention, to provide a consumable.

DETAILED DESCRIPTION OF THE INVENTION

The present invention generally relates to methods of converting crystalline compositions containing Reb M and Reb D with poor aqueous solubility to powders with improved aqueous solubility by freeze drying.

The present invention also generally relates to freeze dried powders produced by the methods disclosed herein, as well as methods of preparing consumables, such as beverages, using said freeze dried powder.

I. Definitions

"Consumables," as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

"Crystalline", as used herein, refers to material with a regular ordered internal structure at the molecular level. Crystalline material gives distinct X-ray diffraction patterns with defined peaks and is birefringent. This is contrasted with amorphous material, which lacks sharp peaks in X-ray diffraction patterns (indicating a lack of long range order at the molecular level) and lacks birefringence.

"Total Steviol Glycoside Content", as used herein, refers to the sum of all steviol glycosides' in a given composition or mixture by weight.

II. Freeze Drying Methods

In one embodiment, a method of preparing a freeze dried powder with improved aqueous solubility comprises (a) combining (i) a crystalline composition comprising Reb M and Reb D and (ii) water to provide a mixture; (b) heating the mixture to provide a solution; and (c) freeze drying the solution to provide a freeze dried powder comprising Reb M and Reb D.

In exemplary embodiments, Reb M and Reb D are the major components of the crystalline composition, i.e. Reb M and Reb D are present by weight in the greatest amount compared to other components of the composition, e.g. steviol glycosides.

The crystalline composition comprises at least about 10% Reb M by weight, such as, for example, at least about 15% Reb M, at least about 20% Reb M, at least about 30% Reb M, at least about 40% Reb M, at least about 50% Reb M, at least about 60% Reb M, at least about 70% Reb M, at least about 80% Reb M, at least about 90% Reb M, at least about 95% Reb M or at least about 97% Reb M.

In exemplary embodiments, the crystalline composition comprises at least about 75% Reb M by weight, such as, for example, at least about 80% Reb M, at least about 85% Reb M or about 90% Reb M. In a particular embodiment, the crystalline composition comprises from about 75% Reb M to about 90% Reb M, from about 75% Reb M to about 85% Reb M, from about 75% Reb M to about 80% Reb M, from about 80% Reb M to about 90% Reb M, from about 80% Reb M to about 85% Reb M or from about 85% Reb M to about 90% Reb M.

The crystalline composition further comprises at least about 10% Reb D by weight, such as, for example, at least about 20% by weight, at least about 30% by weight, at least about 40% by weight, at least about 50% by weight, at least about 60% by weight, at least about 70% by weight or at least about 80% by weight.

In exemplary embodiments, the crystalline composition comprises at least about 75% Reb M by weight and at least about 10% Reb D by weight, such as, for example, at least about 75% Reb M by weight at least about 15% Reb D by weight, at least about 75% Reb M by weight and at least about 20% Reb D by weight, at least about 80% Reb M by weight and at least about 10% Reb D by weight, at least about 80% Reb M by weight and at least about 15% Reb D by weight or at least about 85% Reb M and at least about 10% Reb D by weight.

In exemplary embodiments, the crystalline composition comprises from about 75% to about 90% Reb M by weight and from about 10% to about 25% Reb D by weight. In a particular embodiment, the crystalline composition comprises from about 75% to about 85% Reb M by weight and from about 15% to about 25% Reb D by weight. In a still further particular embodiment, the crystalline composition comprises from about 75% to about 80% Reb M by weight and about 10% to about 15% Reb D by weight. In a yet further particular embodiment, the crystalline composition comprises from about 80% to about 85% Reb M by weight and about 15% to about 20% Reb D by weight.

In another embodiment, the crystalline composition comprises from about 10% to about 85% Reb M by weight and from about 10 to about 85% Reb D by weight. In a particular embodiment, the crystalline composition comprises a composition comprising from about 10% to about 85% Reb M by weight and from about 10 to about 85% Reb D by weight.

In other exemplary embodiments, the crystalline composition comprises from about 20% to about 30% Reb M and about 60% to about 70% Reb D. In a particular embodiment, the crystalline composition comprises a composition comprising from about 20% to about 30% Reb M and about 60% to about 70% Reb D.

In the present embodiments, the total steviol glycoside content of the crystalline composition is about 95% by weight or greater, such as, for example, about 97% by weight or greater or about 99% by weight or greater.

The crystalline compositions can further include other steviol glycosides that contribute to the total steviol glycoside content. Typically, the percentage of another steviol glycoside is below 20%, more generally 10%, or generally below 5% of the total steviol glycoside content.

Exemplary steviol glycosides include, but are not limited to, rebaudioside A, rebaudioside N, rebaudioside O, rebaudioside E, steviolmonoside, steviolbioside, rubusoside, dulcoside B, dulcoside A, rebaudioside B, rebaudioside G, stevioside, rebaudioside C, rebaudioside F, rebaudioside I, rebaudioside H, rebaudioside L, rebaudioside K, rebaudioside J, rebaudioside W, rebaudioside Z1, rebaudioside Z2, rebaudioside M2, rebaudioside D2, rebaudioside D3, synthetic steviol glycosides, e.g. enzymatically glucosylated steviol glycosides and combinations thereof. These steviol glycosides may come from *stevia* leaf extract, bioconversion of steviol glycosides or via fermentation.

In particular embodiments, the crystalline composition further comprises rebaudioside A.

In other exemplary embodiments, the crystalline composition comprises rebaudiosides D, M, A, N, O and E, wherein the total steviol glycoside content is about 95% or greater by weight on a dry basis. In a particular embodiment, Reb D accounts for from about 55% to about 70% of the total steviol glycoside content by weight, Reb M accounts for from about 18% to about 30% total steviol glycoside content by weight, rebaudioside A accounts for from about 0.5% to about 4% of the steviol glycoside content by weight, rebaudioside N accounts for from about 0.5% to about 5% of the steviol glycoside content by weight, rebaudioside O accounts for from about 0.5% to about 5% of the total steviol glycoside content by weight and rebaudioside E accounts for from about 0.2% to about 2% of the total steviol glycoside content by weight.

In a more particular embodiment, rebaudiosides D, M, A, N, O and E account for at least about 90% total steviol glycoside content by weight.

In a yet further embodiment, rebaudiosides D and M account for from about 80% to about 90% total steviol glycoside content by weight.

The crystalline compositions of the present invention may further comprise SG95, a mixture of steviol glycosides having greater than 95% total steviol glycoside content by weight, from about 50% to about 60% rebaudioside A by weight and from about 30% to about 50% by weight of other steviol glycosides, e.g. stevioside, rebaudiosides B—F, dulcoside, rubusoside and steviolbioside.

Methods of preparing Reb M compositions are provided in PCT application No. PCT/US16/055142. Briefly, the composition is produced by crystallization of *stevia* extract enriched with rebaudiosides D, M, N and O. The enriched *stevia* extract is crystallized from solution comprising water and at least one organic solvent. The organic solvent is selected from the group including methanol, ethanol, n-propanol, iso-propanol, butanol, acetone, or any other organic solvent known to art. In a particular embodiment, the organic solvent is ethanol.

In enriched *stevia* extract, the relative content of rebaudiosides D, M, N and O (calculated relative to total steviol glycosides content) is higher than the relative content of rebaudiosides D, M, N and O (calculated relative to total steviol glycosides content) in the *stevia* leaves used as raw material. Enriched *stevia* extract is obtained from dried *stevia* leaves according to methods described in U.S. Pat. No. 8,981,081, #9,562,064, #9,169,285, U.S. patent application Ser. No. 14/362,275, #14/613,615, #14/615,888, PCT applications #PCT/US12/70562 and #PCT/US14/031129.

The crystalline composition can be produced from *stevia* leaf extract, bioconversion of *stevia* leaf extract and/or fermentation of glucose.

The crystalline composition is combined with water to provide a mixture. The amount of water can vary, but typically provides a mixture having a solids content from about 5 wt. % to about 30 wt. %, such as, for example, from about 5 wt. % to about 25 wt. %, from about 5 wt. % to about 20 wt. %, from about 5 wt. % to about 15 wt. %, from about 5 wt. % to about 10 wt. %, from about 10 wt. % to about 30 wt. %, from about 10 wt. % to about 20 wt. %, from about 10 wt. % to about 15 wt. %, from about 15 wt. % to about 30 wt. %, from about 15 wt. % to about 25 wt. %, from about 15 wt. % to about 20 wt. %, from about 20 wt. % to about 30 wt. % and from about 20 wt. % to about 25 wt. %.

In exemplary embodiments, water is the only solvent.

In other embodiments, the crystalline composition is combed with water and a food-grade alcohol.

The mixture is typically heated at a temperature and time sufficient to dissolve the crystalline composition and provide a clear solution, as determined by, e.g. visual inspection.

In one embodiment, the mixture is heated between about 70° C. and about 100° C., such as, for example, from about 70° C. to about 98° C., from about 70° C. to about 95° C., from about 70° C. to about 93° C., from about 70° C. to about 90° C., from about 70° C. to about 85° C., and from about 70° C. to about 80° C.

In a more particular embodiment, the mixture is heated between about 80° C. and about 100° C., such as, for example, from about 80° C. to about 98° C., from about 80° C. to about 95° C., from about 80° C. to about 93° C., from about 80° C. to about 90° C., from about 80° C. to about 85° C., from about 85° C. to about 98° C., from about 85° C. to about 95° C., from about 85° C. to about 93° C., from about 85° C. to about 90° C., from about 90° C. to about 98° C., from about 90° C. to about 95° C. and from about 90° C. to about 93° C.

The mixture is typically heated between about 1 and about 60 minutes, such as, for example, from about 1 to about 5 minutes, from about 1 to about 10 minutes, from about 1 to about 20 minutes, from 1 to about 30 minutes, from about 10 to about 60 minutes, from about 20 to about 60 minutes, from about 30 to about 60 minutes, from about 40 to about 60 minutes and from about 50 to about 60 minutes.

Prolonged heating can result in undesirable decomposition and loss of yield. As such, care should be taken not to boil and/or reflux solvent such that the solution becomes concentrated. Accordingly, in exemplary embodiments, heating is minimized to just what is necessary to prepare a solution; the solution is then directly freeze dried. In a particular embodiment, the composition is heated as described above for about 45 minutes or less, such as, for example, about 30 minutes or less, about 20 minutes or less, about 10 minutes or less, about 5 minutes or less, or about 3 minutes or less.

Once the crystalline composition is dissolved, the solution is freeze dried to remove the solvent and provide a freeze dried powder. In exemplary embodiments, the solution is not allowed to cool before freeze drying.

Freeze drying processes are two-fold and contain a rapid freezing step followed by a drying step. In some embodiments, a lyophilizer is used for freeze drying.

The solution can be frozen by any method known to those of skill in the art including, but not limited to, various liquid nitrogen-based techniques. Exemplary techniques include, but are not limited to, direct surface freezing, direct liquid nitrogen spraying, direct liquid nitrogen immersion, secondary circuit cooling using a heat-transfer fluid, and gaseous nitrogen cooling.

The solution should be frozen below the eutectic point of the crystalline composition. In one embodiment, the solution is frozen to below about −5° C., or below about −10° C.

Freezing provides frozen pellets, which are then sublimated (i.e. dried) at a low temperature under reduced pressure to remove the water and optionally food grade alcohol. This can be done in a batch or continuous freeze dryer.

The amount of time for freeze drying can vary depending on sample size and amount of solvent used. In one embodiment, the sample is freeze dried for at least 3 hours, such as, for example, about at least about 5 hours, at least about 10 hours, at least about 15 hours, at least about 20 hours or at least about 24 hours.

In exemplary embodiments, e.g. large-scale batch runs, the combining step is done in a slurry tank. In one embodiment, the slurry tank typically contains from about 5 wt. % to about 30 wt. % solids and is maintained a temperature from about 10° C. to about 60° C. The mixture is then pumped out of the slurry tank and through a heat exchanger at an elevated temperature (e.g. about 70° C.), with an exit temperature from about 80'C to about 100° C., more preferably from about 88° C. to about 100° C. This heating dissolves the crystalline composition, providing a solution. The solution is then freeze dried, typically in a two-part process, as described above.

The solution can be frozen by any known means including, but not limited to, liquid nitrogen-based techniques and cold surface cooling with coolants, e.g. ethanol. Freezing provides frozen pellets, which are then sublimated in a batch or continuous freeze dryer to provide freeze dried powder.

The freeze dried powder produced by the methods disclosed herein has increased aqueous solubility compared to the aqueous solubility of the starting material, i.e. crystalline composition. In one embodiment, the aqueous solubility of the powder is at least about 0.5%, such as, for example, at least about 1%, at least about 1.5% or at least about 2%.

In some embodiments, the freeze dried powder is at least about 6 times as soluble compared to the crystalline composition, such as, for example, at least about 10 times, at least about 20 times, at least about 30 times or at least about 40 times. In particular embodiments, the freeze dried powder is about 6 times, about 10 times, or about 40 times as soluble compared to the crystalline composition.

A number of methods are known in the art for determining aqueous solubility. In one such method, solubility can be determined by adding sample to a solvent (here, water) in aliquots. The mixture is generally vortexed and/or sonicated between additions to facilitate dissolution. Complete dissolution of the test material is determined by visual inspection. Solubility is then calculated based on the amount of sample that can be dissolved in the amount of solvent×100 (% w/w).

In exemplary embodiments, the yield of the process is typically about 85% or greater, such as, for example, about 90% or greater, about 95% or greater, about 97% or greater, about 98% or greater, or about 99% or greater.

In certain embodiments, the powder is produced in the absence of a dextrin, including cyclodextrin and maltodextrin. In certain embodiments, the powder is free of erythritol.

III. Compositions

Compositions of the present invention comprise a freeze dried powder produced by the methods described herein. In certain embodiments, the compositions can be used to create further compositions for use as a sweetener or as part of a sweetener or flavor system in a consumable product.

In certain embodiments, the freeze dried composition of the present invention can be used to generate consumables. Consumables include, but are not limited to, pharmaceutical compositions, edible gel mixes and compositions, dental compositions, foodstuffs (confections, condiments, chewing gum, cereal compositions, baked goods, dairy products, and tabletop sweetener compositions) beverages and beverage products.

In certain embodiments, a sweetener or flavor system includes a freeze dried composition as described herein and at least one additional substance. The at least one additional substance can be, e.g. a sweetener, additive and/or functional ingredient. The sweetener can be a natural sweetener, a natural high potency sweetener or synthetic sweetener.

As used herein, the phrase "natural high potency sweetener" refers to any sweetener found naturally in nature and characteristically has a sweetness potency greater than sucrose, fructose, or glucose, yet has less calories. The natural high potency sweetener can be provided as a pure compound or, alternatively, as part of an extract. As used herein, the phrase "synthetic sweetener" refers to any composition which is not found naturally in nature and characteristically has a sweetness potency greater than sucrose, fructose, or glucose, yet has less calories.

In one embodiment, the sweetener is a carbohydrate sweetener. Suitable carbohydrate sweeteners include, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable sweeteners include siamenoside, monatin and its salts (monatin SS, RR, RS, SR), curculin, mogrosides, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In one embodiment, the sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the sweetener is a rare sugar selected from allulose, gulose, kojibiose, sorbose, lyxose, ribulose, xylose, xylulose, D-allose, L-ribose, D-tagatose, L-glucose, L-fucose, L-arabinose, turanose and combinations thereof.

Exemplary functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In certain embodiments, the functional ingredient is at least one saponin. As used herein, the at least one saponin may comprise a single saponin or a plurality of saponins as a functional ingredient for the composition provided herein. Saponins are glycosidic natural plant products comprising an aglycone ring structure and one or more sugar moieties. Non-limiting examples of specific saponins for use in particular embodiments of the invention include group A acetyl saponin, group B acetyl saponin, and group E acetyl saponin. Several common sources of saponins include soybeans, which have approximately 5% saponin content by dry weight, soapwort plants (Saponaria), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662.

In certain embodiments, the functional ingredient is at least one antioxidant. As used herein, "antioxidant" refers to any substance which inhibits, suppresses, or reduces oxidative damage to cells and biomolecules.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In one embodiment, the antioxidant is a catechin such as, for example, epigallocatechin gallate (EGCG). In another embodiment, the antioxidant is chosen from proanthocyanidins, procyanidins or combinations thereof. In particular embodiments, the antioxidant is an anthocyanin. In still other embodiments, the antioxidant is chosen from quercetin, rutin or combinations thereof. In one embodiment, the antioxidant is reservatrol. In another embodiment, the antioxidant is an isoflavone. In still another embodiment, the antioxidant is curcumin. In a yet further embodiment, the antioxidant is chosen from punicalagin, ellagitannin or combinations thereof. In a still further embodiment, the antioxidant is chlorogenic acid.

In certain embodiments, the functional ingredient is at least one dietary fiber. Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof. Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

In certain embodiments, the functional ingredient is at least one fatty acid. As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, MD), OmegaPure (from Omega Protein, Houston, TX), Marinol C-38 (from Lipid Nutrition, Channahon, IL), Bonito oil and MEG-3 (from Ocean Nutrition, Dartmouth, NS), Evogel (from Symrise, Holzminden, Germany), Marine Oil, from tuna or salmon (from Arista Wilton, CT), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

In certain embodiments, the functional ingredient is at least one vitamin. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C.

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins. In some embodiments, the vitamin is a fat-soluble vitamin chosen from vitamin A, D, E, K and combinations thereof. In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

In certain embodiments, the functional ingredient is glucosamine, optionally further comprising chondroitin sulfate.

In certain embodiments, the functional ingredient is at least one mineral. Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In one embodiment, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In a particular embodiment, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in one embodiment, the minerals may be in their ionic form, having either a positive or negative charge. In another embodiment, the minerals may be in their molecular form. For example, sulfur and phosphorous often are found naturally as sulfates, sulfides, and phosphates.

In certain embodiments, the functional ingredient is at least one preservative. In particular embodiments, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone. In one embodiment, the preservative is a sulfite. Sulfites include, but are not limited to, sulfur dioxide, sodium bisulfite, and potassium hydrogen sulfite. In another embodiment, the preservative is a propionate. Propionates include, but are not limited to, propionic acid, calcium propionate, and sodium propionate. In yet another embodiment, the preservative is a benzoate. Benzoates include, but are not limited to, sodium benzoate and benzoic acid. In still another embodiment, the preservative is a sorbate. Sorbates include, but are not limited to, potassium sorbate, sodium sorbate, calcium sorbate, and sorbic acid. In a still further embodiment, the preservative is a nitrate and/or a nitrite. Nitrates and nitrites include, but are not limited to, sodium nitrate and sodium nitrite. In another embodiment, the at least one preservative is a bacteriocin, such as, for example, nisin. In still another embodiment, the preservative is ethanol. In yet another embodiment, the preservative is ozone. Non-limiting examples of antienzymatics suitable for use as preservatives in particular embodiments of the invention include ascorbic acid, citric acid, and metal chelating agents such as ethylenediaminetetraacetic acid (EDTA).

In certain embodiments, the functional ingredient is at least one hydration agent. In a particular embodiment, the hydration agent is an electrolyte. Non-limiting examples of electrolytes include sodium, potassium, calcium, magnesium, chloride, phosphate, bicarbonate, and combinations thereof. Suitable electrolytes for use in particular embodiments of this invention are also described in U.S. Pat. No. 5,681,569. In one embodiment, the electrolyte is obtained from the corresponding water-soluble salt. Non-limiting examples of salts include chlorides, carbonates, sulfates, acetates, bicarbonates, citrates, phosphates, hydrogen phosphates, tartrates, sorbates, citrates, benzoates, or combinations thereof. In other embodiments, the electrolyte is provided by juice, fruit extracts, vegetable extracts, tea, or tea extracts.

In another particular embodiment, the hydration agent is a carbohydrate to supplement energy stores burned by muscles. Suitable carbohydrates for use in particular embodiments of this invention are described in U.S. Pat. Nos. 4,312,856, 4,853,237, 5,681,569, and 6,989,171. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration agent is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration agent is a glycerol solution to enhance exercise endurance. The ingestion of a glycerol containing solution has been shown to provide beneficial physiological effects, such as expanded blood volume, lower heart rate, and lower rectal temperature.

In certain embodiments, the functional ingredient is chosen from at least one probiotic, prebiotic and combination thereof. The probiotic is a beneficial microorganism that affects the human body's naturally-occurring gastrointestinal microflora. Examples of probiotics include, but are not limited to, bacteria of the genus Lactobacilli, Bifidobacteria, Streptococci, or combinations thereof, that confer beneficial effects to humans. In particular embodiments of the invention, the at least one probiotic is chosen from the genus Lactobacilli. According to other particular embodiments of this invention, the probiotic is chosen from the genus Bifidobacteria. In a particular embodiment, the probiotic is chosen from the genus *Streptococcus*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the embodiments of this invention, include, without limitation, mucopolysaccharides, oligosaccharides, polysaccharides, amino acids, vitamins, nutrient precursors, proteins and combinations thereof. According to a particular embodiment of this invention, the prebiotic is chosen from dietary fibers, including, without limitation, polysaccharides and oligosaccharides. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalactooligosaccharides, and xylo-oligosaccharides. In other embodiments, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

In certain embodiments, the functional ingredient is at least one weight management agent. As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrients selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment, the weight management agent is a dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In another particular embodiment, the weight management agent is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from *Gymnema sylvestre*, Kola Nut, Citrus Auran tium, Yerba Mate, *Griffonia simplicifolia*, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In one embodiment, the herbal extract is derived from a plant of the genus *Hoodia*. A sterol glycoside of *Hoodia*, known as P57, is believed to be responsible for the appetite-suppressant effect of the *Hoodia* species. In another embodiment, the herbal extract is derived from a plant of the genus *Caralluma*, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X. In another embodiment, the at least one herbal extract is derived from a plant of the genus *Trichocaulon*. *Trichocaulon* plants are succulents that generally are native to southern Africa, similar to *Hoodia*, and include the species *T. pilhferum* and *T. officinale*. In another embodiment, the herbal extract is derived from a plant of the genus *Stapelia* or *Orbea*. Not wishing to be bound by any theory, it is believed that the compounds exhibiting appetite suppressant activity are saponins, such as pregnane glycosides, which include stavarosides A, B, C, D, E, F, G, H, I, J, and K. In another embodiment, the herbal extract is derived from a plant of the genus *Asclepias*. Not wishing to be bound by any theory, it is believed that the extracts comprise steroidal compounds, such as pregnane glycosides and pregnane aglycone, having appetite suppressant effects.

In another particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

In certain embodiments, the functional ingredient is at least one osteoporosis management agent. In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium soucree. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus*, and *Anethum*, as disclosed in U.S. Patent Publication No. 2005/0079232.

In certain embodiments, the functional ingredient is at least one phytoestrogen. Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, *soya* flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover. In certain embodiments, the functional ingredient is at least one long chain primary aliphatic saturated alcohol. Long-chain primary aliphatic saturated alcohols are a diverse group of organic compounds. The term alcohol refers to the fact these compounds feature a hydroxyl group (—OH) bound to a carbon atom. Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In one embodiment, the long-chain primary aliphatic saturated alcohol is a policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

In certain embodiments, the functional ingredient is at least one phytosterol, phytostanol or combination thereof. As used herein, the phrases "stanol", "plant stanol" and "phytostanol" are synonymous. Plant sterols and stanols are present naturally in small quantities in many fruits, vegetables, nuts, seeds, cereals, legumes, vegetable oils, bark of the trees and other plant sources. Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. Non-limiting suitable phytosterols include, but are not limited to, 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. Suitable phytostanols include, but are not limited to, β-sitostanol, campestanol, cycloartanol, and saturated forms of other triterpene alcohols.

Both phytosterols and phytostanols, as used herein, include the various isomers such as the α and β isomers. The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily ascertain the appropriate amount of functional ingredient for each composition.

Exemplary additives include, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, plant extracts, flavonoids, alcohols, polymers and combinations thereof.

In one embodiment, the composition further comprises one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Non-limiting examples of polyols in some embodiments include maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect taste.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in the sweetener composition in an amount effective to provide a concentration from about 10 ppm to about 5,000 ppm when present in a consumable, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable bitter compound additives include, but are not limited to, caffeine, quinine, urea, bitter orange oil, naringin, quassia, and salts thereof.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, New Jersey, U.S.A.), and Sucramask™ (Creative Research Management, Stockton, California, U.S.A.).

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

Suitable alcohol additives include, but are not limited to, ethanol. In particular embodiments, the alcohol additive is present in the consumable in a concentration from about 625 ppm to about 10,000 ppm.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols). The astringent additive is present in the consumable in a concentration from about 10 ppm to about 5,000 ppm.

IV. Methods of Preparing Compositions and Consumables

The present invention also provides methods of preparing compositions and consumables.

In one embodiment, a method of preparing a composition comprises (i) combining a freeze dried powder of the present invention and at least one additional substance selected from the group consisting of sweeteners, additives, functional ingredients, or a combination thereof.

In another embodiment, a method of preparing a consumable comprises (i) providing a consumable matrix and (ii) adding a freeze dried powder described herein to provide a consumable.

In still another embodiment, a method of preparing a consumable comprises (i) providing a consumable matrix and (ii) adding a composition comprising a freeze dried powder described herein to provide a consumable.

As used herein, the term "consumable matrix" refers to a consumable containing all typical ingredients except the sweetener.

In one embodiment, the steviol glycoside concentration in the consumable (provided by the freeze dried powder) is from about 50 ppm to about 600 ppm, such as, for example, from about 100 ppm to about 600 ppm, from about 200 ppm to about 600 ppm, from about 300 ppm to about 600 ppm, from about 400 ppm to about 600 ppm and any range between.

In one embodiment, the consumable is a beverage or beverage product. In a particular embodiment, a method of preparing a beverage comprises (i) providing a beverage matrix and (ii) adding a freeze dried powder described herein to provide a beverage. In another particular embodiment, a method of preparing a beverage comprises (i) providing a beverage matrix and (ii) adding a composition comprising the freeze dried powder described herein to provide a beverage.

"Beverage product", as used herein, is a ready-to-drink beverage, a beverage concentrate, a beverage syrup, or a powdered beverage. Suitable ready-to-drink beverages include carbonated and non-carbonated beverages. Carbonated beverages include, but are not limited to, frozen carbonated beverages, enhanced sparkling beverages, cola, fruit-flavored sparkling beverages (e.g. lemon-lime, orange, grape, strawberry and pineapple), ginger-ale, soft drinks and root beer. Non-carbonated beverages include, but are not limited to, fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts and smoothies.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a matrix, i.e. the basic ingredient in which the ingredients—including the compositions of the present invention—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water.

The beverage or beverage product can further include at least one additional sweetener. Any of the sweeteners detailed herein can be used, including natural, non-natural, or synthetic sweeteners. The beverage or beverage product can contain additives and/or functional ingredients, detailed herein above.

It is contemplated that the pH of the consumable, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage may, for example, range from about 0.01 to about 1.0% by weight of beverage. In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The beverage can be caffeinated or non-caffeinated.

The temperature of a beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz. serving.

The beverage can be a low-calorie beverage that has up to about 40 calories per 8 oz. serving.

The beverage can be a zero-calorie that has less than about 5 calories per 8 oz. serving.

In a particular embodiment, the consumable is a cola beverage. The cola beverage can be a low-, mid- or zero-calorie beverage.

In some embodiments, the cola beverage further comprises allulose and/or erythritol.

In other embodiments, the cola beverage further comprises caffeine.

EXAMPLES

In the following examples, Reb M (>75%) refers to a steviol glycoside mixture containing 80-90% Reb M by weight and 8-18% Reb D by weight. The total steviol glycoside content of the mixture is at least 95%.

Example 1: Freeze Drying of Crystalline Reb M (10% Solution)

The temperature of the freeze dryer was lowered to −20° C. while the Reb M solution was prepared. DI water (135 g) was added to a 250 mL beaker and placed on a hot plate. 15 g of solid Reb M (>75% pure), crystalline form, was added slowly with mixing vortex (stir bar). The hot plate was turned on and the solution was heated to approximately 92° C. and held for approximately 3 minutes until dissolved (visual inspection). The solution was poured into the freeze dryer pan at −20° C. to quench the solution below −10° C. The freeze dryer vacuum was started and allowed to continue for about 20 hours. After the sample was dry, it was warmed to about 20° C. and removed from the freeze dryer. The weight of the recovered powered was 14.8 g, corresponding to greater than 98% product yield.

Example 2: Freeze Drying of Crystalline Reb M (14% Solution)

The temperature of the freeze dryer was lowered to −20° C. while the Reb M solution was prepared. DI water (172 g) was added to a 250 mL beaker and placed on a hot plate. 28 g of Reb M (>75% pure), crystalline form, was added slowly with mixing vortex (stir bar). The hot plate was turned on and the solution was heated to approximately 95° C. and held for approximately 3 minutes until dissolved (visual inspection). The solution was poured into the freeze dryer pan at −20° C. to quench the solution below −10° C. The freeze dryer vacuum was started and allowed to continue for about 24 hours. After the sample was dry, it was warmed to about 20° C. and removed from the freeze dryer. The weight of the recovered powered was 27.7 g, corresponding to greater than 98% product yield.

Example 3: Freeze Drying of Crystalline Reb M (20% Solution)

The temperature of the freeze dryer was lowered to −20° C. while the Reb M solution was prepared. DI water (160 g) was added to a 250 mL beaker and placed on a hot plate. 40 g of Reb M (>75% pure), crystalline form, was added slowly with mixing vortex (stir bar). The hot plate was turned on and the solution was heated to approximately 98° C. and held for approximately 3 minutes until dissolved (visual inspection). The solution was poured into the liquid Nitrogen bath at −196° C. to quench the solution below −20° C. The freeze dryer vacuum was started and allowed to continue for about 24 hours. After the sample was dry, it was warmed to about 20° C. and removed from the freeze dryer. The weight of the recovered powered was 39.5 g, corresponding to greater than 98% product yield.

Example 4: Freeze Drying of Crystalline Reb M (30% Solution)

The temperature of the freeze dryer was lowered to −20° C. while the Reb M solution was prepared. DI water (140 g) was added to a 250 mL beaker and placed on a hot plate. 60 g of Reb M (>75% pure), crystalline form, was added slowly with mixing vortex (stir bar). The hot plate was turned on and the solution was heated to approximately 100° C. and held for approximately 3 minutes until dissolved (visual inspection). The solution was poured into the liquid Nitrogen bath at −196° C. to quench the solution below −20° C. The freeze dryer vacuum was started and allowed to continue for about 24 hours. After the sample was dry, it was warmed to about 20° C. and removed from the freeze dryer. The weight of the recovered powered was 59.2 g, corresponding to greater than 98% product yield.

Example 5: Solubility Testing of Freeze Dried Powder

The solubility of the freeze dried powder produced in Example 1 was compared to the solubility of the crystalline form (~0.15%).

49.25 g of DI water was weighed into a 250 mL beaker with stirring. 0.75 g of the freeze dried powder was added to the beaker slowly with stirring over approximately 2 minutes. The sample completely dissolved by visual inspection.

The aqueous solubility of the freeze dried powder (1.5%) is superior to the aqueous solubility of the crystalline form (~0.15%).

The solubility of the freeze dried powder produced in Example 2 was also compared to the solubility of the crystalline form (~0.15%).

99.5 g of DI water was weighed into a 250 mL beaker with stirring. 1.0 g of the freeze dried powder was added to the beaker slowly with stirring over approximately 2 minutes. The sample completely dissolved by visual inspection.

The aqueous solubility of the freeze dried powder (1.0%) was superior to the aqueous solubility of the crystalline form (~0.15%)

Example 6: Freeze Drying Crystalline Mixture of Reb D and Reb M Mixture (8.3% Solution)

The temperature of the freeze dryer was lowered to −20° C. while the Reb D/Reb M solution was prepared. DI water (61.7 g) was added to a 250 mL beaker and placed on a hot plate. 30 g of food grade alcohol was added to the beaker. 8.3 g of a mixture of Reb D (approximately 60-70 wt. %) and Reb M (approximately 20-30 wt. %), crystalline form, was added slowly with mixing vortex (stir bar). The hot plate was turned on and the solution was heated to approximately 87° C. and held for approximately 3 minutes until dissolved (visual inspection). The solution was poured into the freeze dryer pan at −20° C. to quench the solution below −10° C. The freeze dryer vacuum was started and allowed to continue for about 20 hours. After the sample was dry, it was warmed to about 20° C. and removed from the freeze dryer. The weight of the recovered powered was 8.1 g, corresponding to greater than 97% product yield.

Example 7: Freeze Drying Crystalline Mixture of Reb D and Reb M Mixture (10 wt %) and SG95 (5 wt %)

The temperature of the freeze dryer was lowered to −20° C. while the solution was prepared. DI water (80.0 g) was added to a 250 mL beaker and placed on a hot plate. 10 g of food grade alcohol was added to the beaker. 9.5 g of a mixture of Reb D (approximately 60-70 wt. % of the mixture) and Reb M (approximately 20-30 wt. % of the mixture), crystalline form, and 0.5 g SG95 (50-60 wt. % reb A and 30-50 wt. % of mixture of stevioside, rebaudioside B—F, Dulcoside, rubusoside, steviolbioside, total steviol glycoside content>95%) was added slowly with mixing vortex (stir bar). The hot plate was turned on and the solution was heated to approximately 98° C. and held for approximately 3 minutes until dissolved (visual inspection). The solution was poured into the freeze dryer pan at −20° C. to quench the solution below −10° C. The freeze dryer vacuum was started and allowed to continue for about 20 hours. After the sample was dry, it was warmed to about 20° C. and removed from the freeze dryer. The weight of the recovered powered was 9.9 g, corresponding to greater than 98% product yield.

Example 8: Solubility Testing of Freeze Dried Mixtures of Reb D and Reb M Powders The solubility of the freeze dried mixture of Reb D and Reb M powder produced in Example 6 was compared to the solubility of the crystalline form of the mixture (~0.05%).

In a first experiment, 49.75 g of DI water was weighed into a 250 mL beaker with stirring. 0.25 g of the freeze dried powder was added to the beaker slowly with stirring over approximately 2 minutes. The sample completely dissolved by visual inspection.

In a second experiment, 49.0 g of DI water was weighed into a 250 mL beaker with stirring. 1.0 g of the freeze dried powder was added to the beaker slowly with stirring over approximately 2 minutes. The sample completely dissolved by visual inspection.

The aqueous solubility of the freeze dried powders (0.5% and 2.0% for the first and second experiments, respectively) was superior to the aqueous solubility of the crystalline form of the mixture (~0.05%).

The solubility of the freeze dried powder produced in Example 7 was also measured.

In a first experiment, 49.75 g of DI water was weighed into a 250 mL beaker with stirring. 0.25 g of the freeze dried powder was added to the beaker slowly with stirring over approximately 2 minutes. The sample completely dissolved by visual inspection.

In a second experiment, 49.0 g of DI water was weighed into a 250 mL beaker with stirring. 1.0 g of the mixture of the freeze dried powder was added to the beaker slowly with stirring over approximately 2 minutes. The sample completely dissolved by visual inspection.

The aqueous solubility of the freeze dried powders (0.5% and 2.0% for the first and second experiments, respectively) was superior to the aqueous solubility of the crystalline form of the mixture (~0.05%).

The invention claimed is:

1. A method of preparing a freeze dried powder with improved aqueous solubility comprising:
   a. preparing a mixture consisting of water and a crystalline steviol glycoside composition consisting essentially of about 75% to about 90% Reb M by weight, about 10% to about 25% Reb D by weight; and wherein the mixture has a solids content from about 10% to about 30% by weight;
   b. heating the mixture to a temperature from about 70° C. to 98° C. for a time sufficient to dissolve the crystalline composition and provide a clear solution; and
   c. freeze drying the clear solution to provide a freeze dried powder.

2. The method of claim 1, wherein step a. further comprises adding a food grade alcohol.

3. The method of claim 1, wherein the freeze drying is performed with a lyophilizer.

4. The method of claim 1, wherein freeze drying comprises:
   (i) freezing the solution to provide frozen pellets; and
   (ii) sublimating the frozen pellets to provide a freeze dried powder.

5. The method of claim 1, wherein step a. is performed in a slurry tank.

6. The method of claim 5, wherein step b. is performed with a heat exchanger.

7. The method of claim 6, wherein freeze drying comprises:
   (i) freezing the solution to provide frozen pellets; and
   (ii) sublimating the frozen pellets using a continuous or batch freeze dryer.

8. The method of claim 1, wherein the freeze dried powder has an aqueous solubility of at least about 0.5%.

9. A method of preparing a consumable comprising (i) providing a consumable matrix and (ii) adding a freeze dried powder produced by the method of claim 1, or a composition comprising a freeze dried powder produced by the method of claim 1, to provide a consumable, wherein the freeze dried powder has an aqueous solubility of at least about 0.5%.

10. The method of claim 9, wherein the freeze dried powder has an aqueous solubility of at least about 1.0%.

11. The method of claim 9, wherein the consumable is a beverage or beverage product.

12. A freeze dried powder produced by the method of claim 1.

13. The method of claim 1, wherein the mixture is heated in step b. for 45 minutes or less.

14. The method of claim 1, wherein the mixture in step b. is not boiled or refluxed.

15. The method of claim 1, wherein the heating is minimized to what is necessary to provide a clear solution, and the clear solution is then directly freeze dried.

* * * * *